US010918443B2

(12) United States Patent
Ikuma et al.

(10) Patent No.: US 10,918,443 B2
(45) Date of Patent: Feb. 16, 2021

(54) NAVIGATION SYSTEM AND OPERATION METHOD OF NAVIGATION SYSTEM

(71) Applicant: OLYMPUS CORPORATION, Tokyo (JP)

(72) Inventors: Soichi Ikuma, Akishima (JP); Tatsuro Yamamoto, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 927 days.

(21) Appl. No.: 15/402,634

(22) Filed: Jan. 10, 2017

(65) Prior Publication Data
US 2017/0112578 A1    Apr. 27, 2017

Related U.S. Application Data

(63) Continuation of application No. PCT/JP2015/062831, filed on Apr. 28, 2015.

(30) Foreign Application Priority Data

Jul. 15, 2014   (JP) ................................. 2014-145312

(51) Int. Cl.
A61B 34/20   (2016.01)
A61B 1/00    (2006.01)
A61B 1/04    (2006.01)

(52) U.S. Cl.
CPC .............. *A61B 34/20* (2016.02); *A61B 1/00* (2013.01); *A61B 1/00009* (2013.01);
(Continued)

(58) Field of Classification Search
CPC .......... A61B 34/20; A61B 34/25; A61B 1/00; A61B 1/00009; A61B 1/00045; A61B 1/00147; A61B 1/04; A61B 1/2676
See application file for complete search history.

(56) References Cited

U.S. PATENT DOCUMENTS

2009/0161927 A1   6/2009   Mori et al.
2013/0257865 A1   10/2013  Kobayashi
2014/0088357 A1   3/2014   Ikuma et al.

FOREIGN PATENT DOCUMENTS

CN    103298407 A    9/2013
CN    103561628 A    2/2014
(Continued)

OTHER PUBLICATIONS

Roberts, Steve, and Roger E. Thornington. "Paediatric bronchoscopy." Continuing Education in Anaesthesia, Critical Care & Pain 5, No. 2 (2005): 41-44.*

(Continued)

*Primary Examiner* — Carolyn A Pehlke
(74) *Attorney, Agent, or Firm* — Scully, Scott, Murphy & Presser, P.C.

(57) ABSTRACT

A navigation system includes an alignment unit configured to generate corrected position information in which position information of a viewpoint of an endoscope that is inserted in a subject is aligned with a three-dimensional image of a luminal organ, a determination unit configured to determine performance/non-performance of observation of a branch conduit based on the corrected position information, a target setting unit configured to set one unobserved conduit as a first target region based on a distance between the position information of the current viewpoint and the unobserved conduit, and a navigation information generation unit configured to generate navigation information for the first target region.

8 Claims, 9 Drawing Sheets

(52) U.S. Cl.
CPC ...... *A61B 1/00045* (2013.01); *A61B 1/00147* (2013.01); *A61B 1/04* (2013.01); *A61B 2034/2055* (2016.02)

(56) References Cited

FOREIGN PATENT DOCUMENTS

| | | |
|---|---|---|
| JP | 2004-089483 A | 3/2004 |
| JP | 2005-211535 A | 8/2005 |
| JP | 2005-312770 A | 11/2005 |
| JP | 2008-537730 A | 9/2008 |
| JP | 2009-279251 A | 12/2009 |
| JP | 2011-189074 A | 9/2011 |
| JP | 5378628 B1 | 12/2013 |
| WO | WO 2007/129493 A1 | 11/2007 |
| WO | WO 2013/132880 A1 | 9/2013 |

OTHER PUBLICATIONS

International Search Report dated Jul. 28, 2015 issued in PCT/JP2015/062831.

* cited by examiner

NAVIGATION SYSTEM AND OPERATION METHOD OF NAVIGATION SYSTEM

CROSS REFERENCE TO RELATED APPLICATION

This application is a continuation application of PCT/JP2015/062831 filed on Apr. 28, 2015 and claims benefit of Japanese Application No. 2014-145312 filed in Japan on Jul. 15, 2014, the entire contents of which are incorporated herein by this reference.

BACKGROUND OF THE INVENTION

1. Field of the Invention

The present invention relates to a navigation system configured to construct three-dimensional image information from image information about a subject acquired in advance, to extract a luminal organ, and to generate navigation information, and an operation method of the navigation system.

2. Description of the Related Art

An endoscope apparatus is widely used as a medical endoscope for performing observation of an organ in a body cavity, and for performing medical treatment by using a treatment instrument as necessary, for example. In the case of performing observation or medical treatment by such an endoscope apparatus, an insertion section of an endoscope has to be inserted into a lumen, and a distal end portion of the insertion section has to be made to reach a destination such as a lesion swiftly and accurately.

Accordingly, to cause the insertion section of the endoscope to reach a destination, a navigation technique of displaying a navigation image and performing guidance is conventionally proposed. Such a navigation technique is used for a luminal organ having branched lumina, such as a bronchus or a kidney, among organs in a body cavity.

For example, Japanese Patent Application Laid-Open Publication No. 2011-189074 describes a technique of detecting a bent shape of a bending portion by using an optical fiber sensor or the like, performing fitting processing for the detected bent shape and the shape of a branch conduit where an insertion section is inserted, distinguishing between a branch conduit where the insertion section is inserted and a branch conduit where the insertion section is not inserted at the time of insertion operation of an endoscope, and accurately displaying the insertion state of the insertion section in a bronchus.

Also, Japanese Patent Application Laid-Open Publication No. 2005-211535 describes a technique of specifying an insertion support start point and an insertion support end point on a model image and specifying, on a virtual endoscopic image by a pointer, a branch conduit where an insertion section is to be inserted, to thereby navigate an insertion section distal end position from the insertion support start point to the insertion support end point.

Now, a stone is sometimes formed in a kidney, which is one of organs in the body cavity, and a treatment for removing such a stone is performed by using a treatment instrument or the like protruding from a distal end of an endoscope and by observing the inside of the renal pelvis and the renal calyces by the endoscope.

More specifically, a stone is first broken into small pieces. At this time, broken pieces may be scattered and may enter peripheral renal calyces, and these broken pieces also have to be removed. Accordingly, to check for presence/absence of remaining stones after breaking, the inside of the renal pelvis and the renal calyces are desirably thoroughly observed by the endoscope.

Accordingly, for example, Japanese Patent Application Laid-Open Publication No. 2008-537730 describes a technique of injecting a marking material into an observed renal calyx to allow identification of an unobserved renal calyx so that presence/absence of remaining stones in the renal calyx after breaking of a stone may be thoroughly checked.

SUMMARY OF THE INVENTION

A navigation system according to an aspect of the present invention includes a position information acquisition unit configured to acquire position information of a viewpoint of an endoscope that is inserted in a subject, an alignment unit configured to generate corrected position information in which the position information of the viewpoint acquired by the position information acquisition unit is aligned with a three-dimensional image of a predetermined luminal organ in the subject, a determination unit configured to determine, with respect to a plurality of branch conduits in the predetermined luminal organ, whether each of the plurality of branch conduits is already observed or is still unobserved by the endoscope, based on the corrected position information, a target setting unit configured to set, when a branch conduit determined by the determination unit as unobserved is given as an unobserved conduit, one unobserved conduit as a first target region, based on a distance between the position information of the viewpoint at a current time acquired by the position information acquisition unit and the unobserved conduit, and a navigation information generation unit configured to generate navigation information for the first target region set by the target setting unit.

An operation method of a navigation system according to an aspect of the present invention is an operation method of a navigation system including a position information acquisition unit, an alignment unit, a determination unit, a target setting unit and a navigation information generation unit, the method including acquiring, by the position information acquisition unit, position information of a viewpoint of an endoscope that is inserted in a subject, generating, by the alignment unit, corrected position information in which the position information of the viewpoint acquired by the position information acquisition unit is aligned with a three-dimensional image of a predetermined luminal organ in the subject, determining, by the determination unit, with respect to a plurality of branch conduits in the predetermined luminal organ, whether each of the plurality of branch conduits is already observed or is still unobserved by the endoscope, based on the corrected position information, setting, by the target setting unit, when a branch conduit determined by the determination unit as unobserved is given as an unobserved conduit, one unobserved conduit as a first target region, based on a distance between the position information of the viewpoint at a current time acquired by the position information acquisition unit and the unobserved conduit, and generating, by the navigation information generation unit, navigation information for the first target region set by the target setting unit.

DETAILED DESCRIPTION OF THE PREFERRED EMBODIMENT(S)

Hereinafter, an embodiment of the present invention will be described with reference to the drawings.

First Embodiment

FIGS. 1 to 11 show a first embodiment of the present invention, and show a configuration of an endoscope system 1. In the present embodiment, a navigation system is applied to the endoscope system 1, and navigation is performed at the time of observation of a subject by the endoscope system 1.

Figure 1:
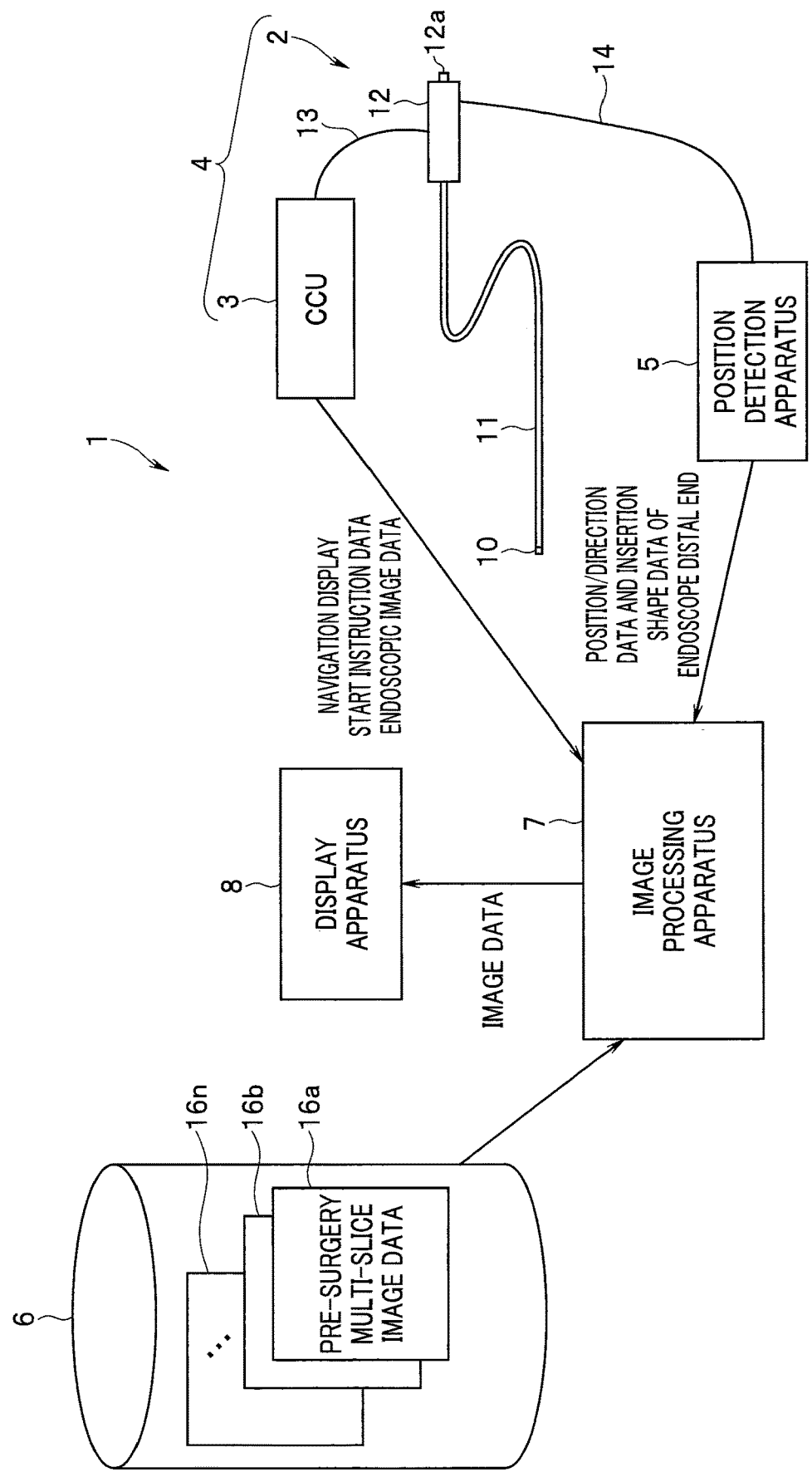
FIG. 1 is a diagram showing a configuration of an endoscope system according to a first embodiment of the present invention.

As shown in FIG. 1, the endoscope system 1 to which the navigation system is applied includes an endoscope apparatus 4 provided with an endoscope 2 and a camera control unit (CCU) 3, a position detection apparatus 5, a server 6, an image processing apparatus 7, and a display apparatus 8.

The endoscope 2 includes a flexible elongated insertion section 11 to be inserted into a subject, an operation section 12 that is continuously provided to a proximal end portion of the insertion section 11, and a cable 13 extending from a side surface of the operation section 12.

A navigation button 12a for generating navigation display start instruction data for starting navigation display is provided to the operation section 12. The navigation button 12a serves also as a navigation start instruction unit to which a command for starting generation of navigation information by a navigation information generation unit 34 described later is inputted. Note that the navigation button 12a does not have to be provided to the operation section 12 of the endoscope 2, and may alternatively be provided as a foot switch or a switch of another structure, for example.

An image pickup system 10 for picking up an image of the inside of a subject is provided at a distal end portion of the insertion section 11. More specifically, the image pickup system 10 includes an objective optical system for forming an optical image of the inside of the subject, and an image pickup device, such as a CCD, for photoelectrically converting the optical image formed by the objective optical system and generating an image pickup signal. The endoscope 2 is connected to the CCU 3 by the cable 13, and the image pickup signal picked up by the image pickup system 10 and the navigation display start instruction data inputted by the navigation button 12a are transmitted to the CCU 3.

The CCU 3 generates endoscopic image data by applying predetermined image processing on the image pickup signal transmitted from the endoscope 2. Also, the CCU 3 receives the navigation display start instruction data inputted by the navigation button 12a.

A plurality of receiving coils, not shown, are provided at predetermined intervals from the distal end portion to the proximal end portion of the insertion section 11 described above. The plurality of receiving coils each output an electrical signal according to the magnetic field generated by the position detection apparatus 5. The endoscope 2 is connected to the position detection apparatus 5 by a cable 14, and each electrical signal outputted from the receiving coils is transmitted to the position detection apparatus 5.

The position detection apparatus 5 as a position information acquisition unit computes and acquires, based on the electrical signal from a receiving coil, among the plurality of receiving coils, provided at the distal end portion of the insertion section 11, position information about a viewpoint of the image pickup system 10 at the distal end of the insertion section 11 inside the subject (the position information includes pieces of information about the three-dimensional position of the viewpoint and the line of sight from the viewpoint). Acquisition of the position information by the position detection apparatus 5 is repeated at constant time intervals, for example.

Moreover, the position detection apparatus 5 computes and acquires insertion shape data indicating the insertion shape of the insertion section 11 based on the electrical signals from the plurality of receiving coils. Note that, in this case, bent shape data is acquired by using the receiving coils, but this is not restrictive, and the bent shape data may also be acquired by using an FBG (fiber Bragg grating) sensor or the like.

The CCU 3, the position detection apparatus 5, and the server 6 described above are connected to the image processing apparatus 7. Among these, the server 6 is connected to the image processing apparatus 7 via a communication line such as a LAN in the hospital, for example.

The CCU 3 transmits, to the image processing apparatus 7, the endoscopic image data generated in the above manner, and the navigation display start instruction data received from the endoscope 2.

The position detection apparatus 5 transmits, to the image processing apparatus 7, the position information about the viewpoint (position and direction data), and the insertion shape data of the insertion section 11.

On the other hand, the server 6 stores pieces of pre-surgery multi-slice image data 16a to 16n that are acquired in advance by CT, MRI, PET or the like before examination is performed by the endoscope system 1, for example. Moreover, the server 6 transmits the pieces of pre-surgery multi-slice image data 16a to 16n to the image processing apparatus 7. Note that, in this case, the image processing apparatus 7 reads the pieces of pre-surgery multi-slice image data 16a to 16n from the server 6, but it is needless to say that the pieces of pre-surgery multi-slice image data 16a to 16n may alternatively be read from a portable recording medium, such as a CD-ROM, storing the pieces of pre-surgery multi-slice image data 16a to 16n.

The image processing apparatus 7 creates image data by performing processing described later based on each piece of data imported from the CCU 3, the position detection apparatus 5, and the server 6.

The image processing apparatus 7 is connected to the display apparatus 8, and the display apparatus 8 receives and displays the image data created by the image processing apparatus 7. As will be described later, the display apparatus 8 is a display unit configured to display a navigation image created by the image processing apparatus 7.

Figure 2:
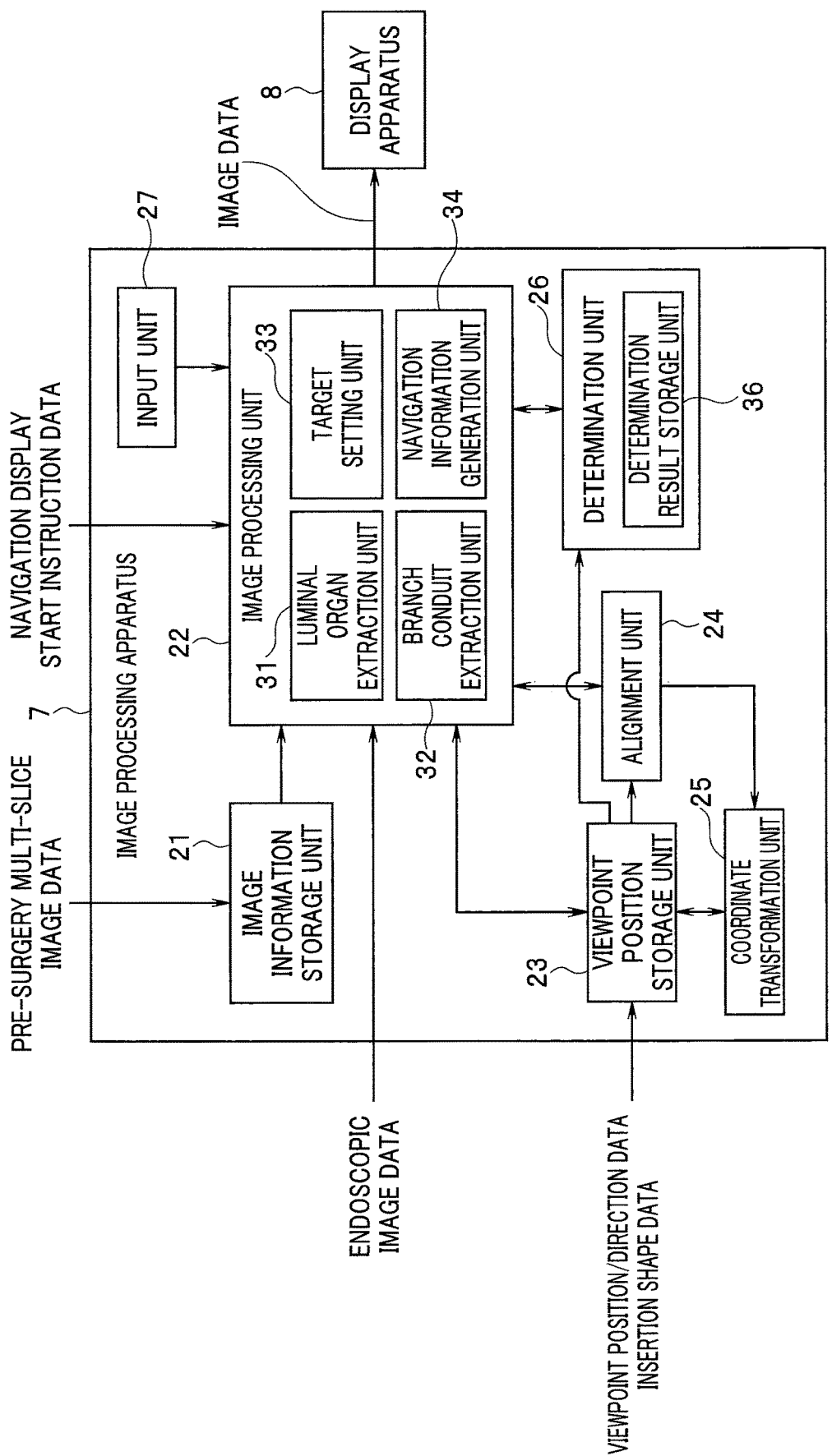
FIG. 2 is a block diagram showing a configuration of an image processing apparatus according to the first embodiment.

Next, FIG. 2 is a block diagram showing a configuration of the image processing apparatus 7.

The image processing apparatus 7 includes an image information storage unit 21, an image processing unit 22, a viewpoint position storage unit 23, an alignment unit 24, a coordinate transformation unit 25, a determination unit 26, and an input unit 27.

The image information storage unit 21 reads from the server 6, and stores, the pieces of pre-surgery multi-slice image data 16a to 16n, which are pieces of image information about a subject acquired in advance for construction of three-dimensional image information.

The viewpoint position storage unit 23 is for storing the position information about a viewpoint acquired by the position detection apparatus 5, and is capable of accumulating pieces of position information at a plurality of time points which are acquired by the position detection apparatus 5 at constant time intervals in the manner described above, for example.

The alignment unit 24 performs alignment of real space coordinates describing the position information of a viewpoint that is acquired by the position detection apparatus 5 and stored in the viewpoint position storage unit 23, and three-dimensional image coordinates describing a predetermined luminal organ that is extracted by a luminal organ extraction unit 31 in a manner described below. Alignment by the alignment unit 24 is performed as calculation of a transformation formula from the real space coordinates to the three-dimensional image coordinates, for example.

Note that the method of alignment is not limited to the method of using the transformation formula mentioned above, and a method of alignment based on detection of the position of a feature point on the body surface of a patient and specification of a feature point on three-dimensional image data as disclosed in Japanese Patent Application Laid-Open Publication No. 2005-312770, or a method of alignment based on matching of an endoscopic image and a virtual endoscopic image as disclosed in Japanese Patent Application Laid-Open Publication No. 2009-279251 may also be adopted, for example.

The coordinate transformation unit 25 transforms, based on the transformation formula calculated by the alignment unit 24, the position and direction data stored in the viewpoint position storage unit 23 to values of three-dimensional data coordinates. Then, the coordinate transformation unit 25 stores position and direction data of the viewpoint after transformation in the viewpoint position storage unit 23 in association with the position and direction data before transformation and a timestamp.

In this manner, the alignment unit 24 and the coordinate transformation unit 25 configure an alignment unit for generating corrected position information by performing alignment of the position information of the viewpoint acquired by the position detection apparatus 5, as the position information acquisition unit, with the three-dimensional image coordinate information of a predetermined luminal organ.

The determination unit 26 determines performance/non-performance of observation of a branch conduit based on position information of a branch conduit extracted by a branch conduit extraction unit 32 from a predetermined region as described later, and the corrected position information after alignment. The determination unit 26 includes a determination result storage unit 36 for cumulatively storing the determination result of the determination unit 26 when the position indicated by the corrected position information received via the viewpoint position storage unit 23 is within the predetermined region. Moreover, the determination unit 26 determines performance/non-performance of observation of a branch conduit every time position information is acquired at constant time intervals, and cumulatively stores the latest determination result in the determination result storage unit 36. Therefore, the storage contents of the determination result storage unit 36 are, for example, "branch conduit 1: unobserved, branch conduit 2: unobserved, . . . , branch conduit n: unobserved" →"branch conduit 1: unobserved, branch conduit 2: observed, . . . , branch conduit n: unobserved", and as the observation proceeds, the observation states of the branch conduits are sequentially changed from "unobserved" to "observed".

The input unit 27 is for performing input of operation to the image processing apparatus 7, and includes a region specification unit configured to be capable of specifying a predetermined region from which a branch conduit is to be extracted by the branch conduit extraction unit 32. A region that is specified by the region specification unit is made a predetermined region which is taken as an observation target. The predetermined region may be arbitrarily specified for a predetermined luminal organ which is extracted by the luminal organ extraction unit 31, and may be a part or all of the predetermined luminal organ.

The image processing unit 22 includes the luminal organ extraction unit 31, the branch conduit extraction unit 32, a target setting unit 33, and the navigation information generation unit 34.

The luminal organ extraction unit 31 reads pieces of image information (pieces of pre-surgery multi-slice image data 16a to 16n) stored in the image information storage unit 21, constructs three-dimensional image information, and furthermore, extracts a predetermined luminal organ from the three-dimensional image information. In this case, the extracted luminal organ is a luminal structure of a kidney, for example. At this time, for example, the luminal organ extraction unit 31 extracts, as a luminal organ 51, a predetermined luminal organ including a ureter 52, a renal pelvis 53, a major calyx 54, minor calyces 55, and renal papillae 56 (and a bladder and a urethra as necessary) (see FIG. 6).

The branch conduit extraction unit 32 extracts a branch conduit, of the predetermined luminal organ, that exists within the predetermined region that is set by the input unit 27 as an observation target. Note that, to perform a thorough examination, the branch conduit extraction unit 32 desirably extracts all the branch conduits that exist within the predetermined region.

The target setting unit 33 sets one of unobserved branch conduits, which are determined by the determination unit 26 as unobserved, as a target branch conduit. Setting of the target branch conduit by the target setting unit 33 is performed based on the latest storage contents of the determination result storage unit 36 described above.

More specifically, the target setting unit 33 sets, as the target branch conduit, an unobserved branch conduit that is closest to a current viewpoint position that is indicated by the corrected position information (preferably, on the distal end side in the insertion direction of the insertion section 11).

Furthermore, when the target branch conduit is determined by the determination unit 26 as unobserved, the target setting unit 33 determines whether the target branch conduit is on the distal end side of the current viewpoint position indicated by the corrected position information, and if the target branch conduit is not on the distal end side of the current viewpoint position, the target branch conduit is updated based on the corrected position information. As will be described later, this is for allowing a new target branch conduit to be set based on the current viewpoint position in a case where a surgeon performs an operation of moving off a navigation route so that appropriate navigation may be performed at all times.

In the case where the target branch conduit is determined by the determination unit 26 as already observed, the navigation information generation unit 34 causes the target setting unit 33 to update the target branch conduit to another one of unobserved branch conduits, and generates navigation information for the target branch conduit. Navigation to unobserved branch conduits is thereby sequentially performed.

In the case of extracting all the branch conduits that exist within the predetermined region by the branch conduit extraction unit 32 described above, the navigation information generation unit 34 determines whether the insertion section 11 may be inserted or not for all the extracted branch conduits, and sequentially generates pieces of navigation information for all the branch conduits for which insertion of the insertion section 11 is determined to be possible.

At this time, the navigation information generation unit 34 may generate the navigation information at constant time intervals according to acquisition of position information by the position detection apparatus 5 that is repeatedly performed at the constant time intervals as described above. The navigation information may thereby be displayed in real time.

As described above, the navigation button 12a is the navigation start instruction unit to which a command for starting generation of navigation information by the navigation information generation unit 34 is inputted, and the navigation information generation unit 34 generates the navigation information from the time point of input of the command to the navigation button 12a. Accordingly, if a surgeon does not operate the navigation button 12a thinking that navigation is not necessary, the navigation information is not generated and is not displayed on the display apparatus 8.

The image processing unit 22 creates image data for display by obtaining a navigation image by superimposing the navigation information generated by the navigation information generation unit 34 on the virtual endoscopic image 42 or the endoscopic image 43, and also using other pieces of display information, and outputs the image data to the display apparatus 8. The display apparatus 8 thereby displays the navigation image.

Figure 6:
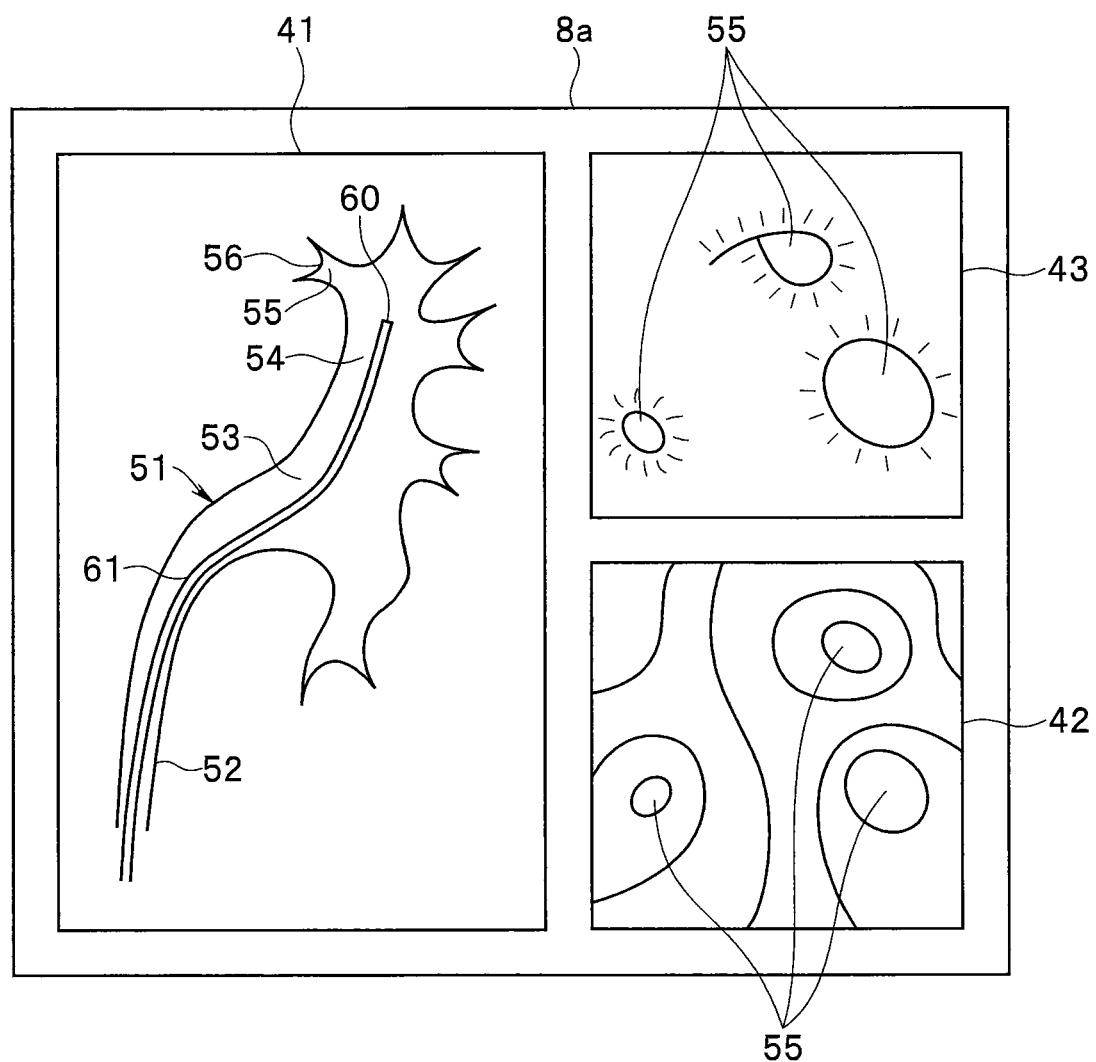
FIG. 6 is a diagram showing example display on a display screen of a display apparatus according to the first embodiment.

Now, FIG. 6 is a diagram showing example display of a display screen 8a of the display apparatus 8. Note that the reference signs in the image displayed on the display screen 8a in FIG. 6 are used as appropriate in the description of the embodiment.

For example, as shown in FIG. 6, a bird's-eye image 41, a virtual endoscopic image 42, and an endoscopic image 43 are displayed on the display screen 8a of the display apparatus 8. The bird's-eye image 41 here is a two-dimensional image of a luminal organ which is three-dimensionally observed when the luminal organ which is constructed as three-dimensional image data is looked down from above. Also, the virtual endoscopic image 42 is a two-dimensional image obtained by observing the luminal organ which is constructed as three-dimensional image data from the viewpoint position of the image pickup system 10. Furthermore, the endoscopic image 43 is a picked-up image that is picked up by the image pickup system 10. Note that the example display shown in FIG. 6 is only an example, and other pieces of information may be displayed, or display of some pieces of information may be omitted.

In the bird's-eye image 41 shown in FIG. 6, the ureter 52, the renal pelvis 53, the major calyx 54, the minor calyces 55, and the renal papillae 56 of the luminal organ 51 are displayed, and moreover, an insertion section image 61 showing the current insertion shape of the insertion section 11 is displayed as navigation. The distal end of the insertion section image 61 is a current viewpoint position 60. In the example shown in the bird's-eye image 41 in FIG. 6, the current viewpoint position 60 is inside the major calyx 54.

In the endoscopic image 43 shown in FIG. 6, openings of a plurality of minor calyces 55 observed from the major calyx 54 are displayed in accordance with the current viewpoint position 60 of the image pickup system 10 inside the major calyx 54.

Furthermore, in the virtual endoscopic image 42, the openings of the plurality of minor calyces 55 which are supposed to be observed from the current viewpoint position 60 of the image pickup system 10 are displayed.

Figure 3:
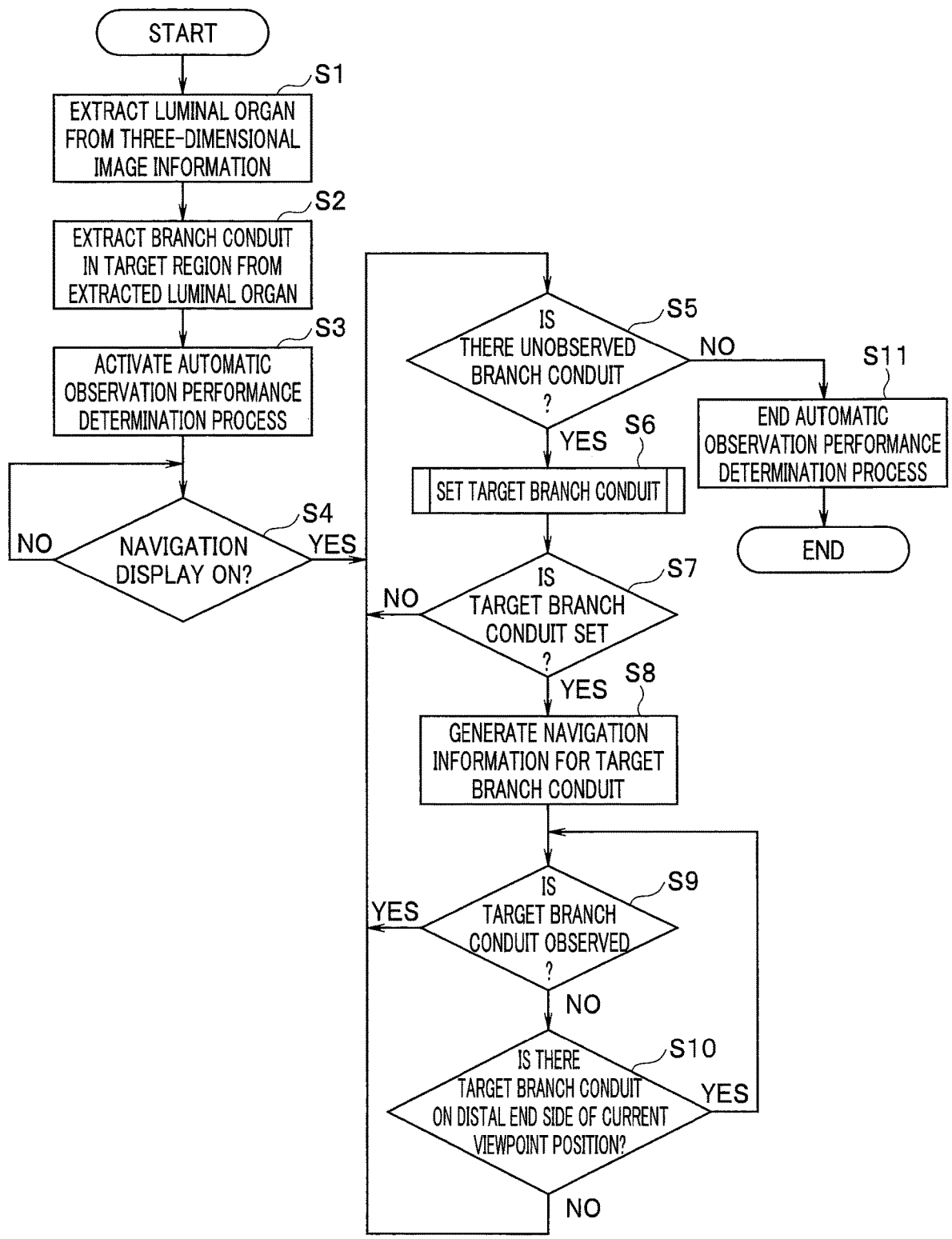
FIG. 3 is a flowchart showing an action of the endoscope system according to the first embodiment.

Next, FIG. 3 is a flowchart showing an action of the endoscope system 1.

When processing shown in FIG. 3 is started, the image processing apparatus 7 accesses the server 6, reads the pieces of pre-surgery multi-slice image data 16a to 16n, and stores the data in the image information storage unit 21. Then, the luminal organ extraction unit 31 constructs three-dimensional image information from the pieces of pre-surgery multi-slice image data 16a to 16n which are stored in the image information storage unit 21, and extracts a predetermined luminal organ from the constructed three-dimensional image information (step S1).

Next, the branch conduit extraction unit 32 extracts, from the predetermined luminal organ extracted by the luminal organ extraction unit 31, a branch conduit existing within a predetermined region which is set by the input unit 27 as an observation target (step S2).

Figure 4:
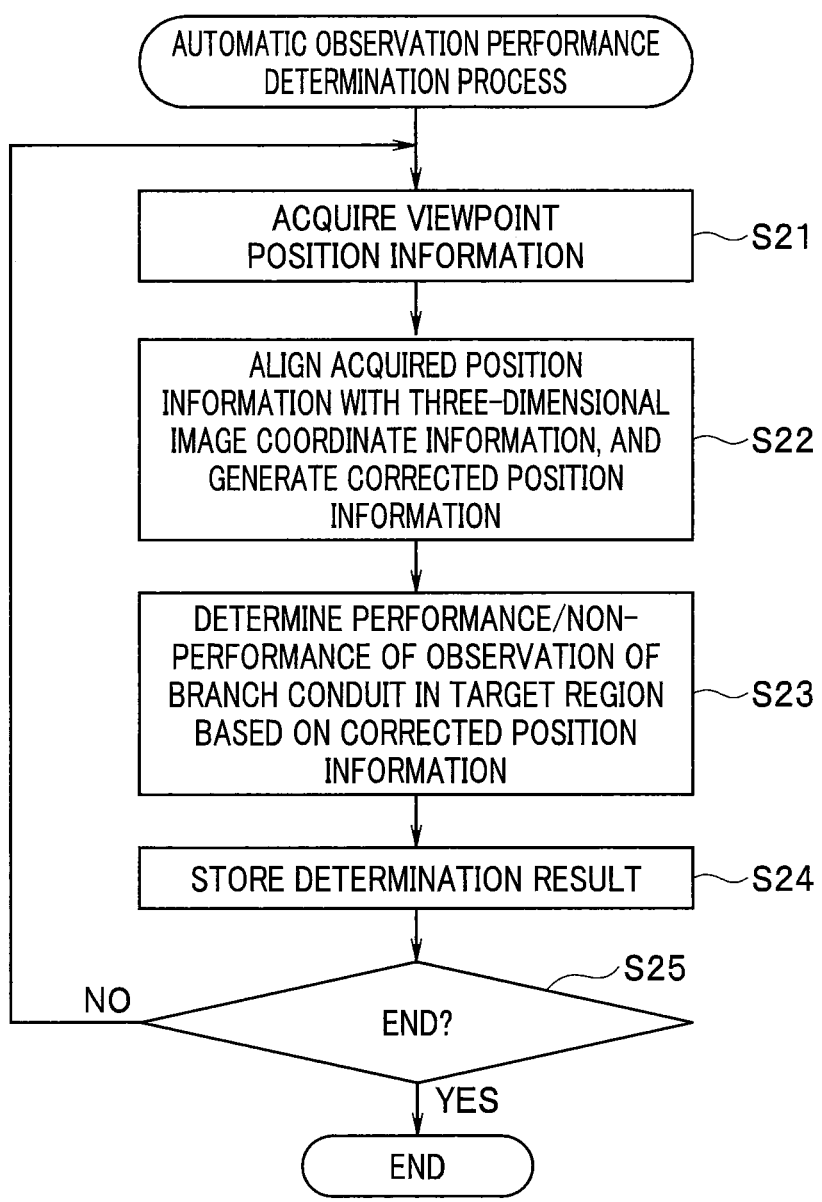
FIG. 4 is a flowchart showing an automatic observation performance determination process by the endoscope system according to the first embodiment.

Then, an automatic observation performance determination process shown in FIG. 4 is activated (step S3).

FIG. 4 is a flowchart showing the automatic observation performance determination process of the endoscope system.

When the process is activated, the latest viewpoint position information is acquired from the position detection apparatus 5, and is stored in the viewpoint position storage unit 23 (step S21).

Next, the acquired latest viewpoint position information is aligned with respect to three-dimensional image coordinate information by the alignment unit 24 and the coordinate transformation unit 25, and the corrected position information is generated (step S22).

Then, the determination unit 26 performs observation performance determination for the branch conduit in the predetermined region, which is the observation target, based on the corrected position information (step S23).

Then, the determination result is cumulatively stored in the determination result storage unit 36 in the manner described above (step S24), and whether to end the process or not is determined based on, for example, whether a process end signal is received or not (step S25).

Here, if end is not determined, the processing returns to step S21, and the next latest viewpoint position information is acquired and the processing as described above is performed, and if end is determined, the process is ended.

By performing the processing described above, the latest information regarding whether each branch conduit in the predetermined region is already observed or not is stored in the determination result storage unit 36.

Returning to description of FIG. 3, after the automatic observation performance determination process is activated in step S3, operation of the navigation button 12a to navigation display on is awaited (step S4). The automatic observation performance determination process activated in step S3 is continued in parallel also during standby for the operation of switching on the navigation display.

When the operation of switching on the navigation display is determined in step S4 to have been performed, whether or not an unobserved branch conduit exists within the predetermined region, which is the observation target, is determined based on the latest determination result of the automatic observation performance determination process stored in the determination result storage unit 36 (step S5).

If, at this time, that an unobserved branch conduit exists is determined, target branch conduit setting processing is performed (step S6).

Figure 5:
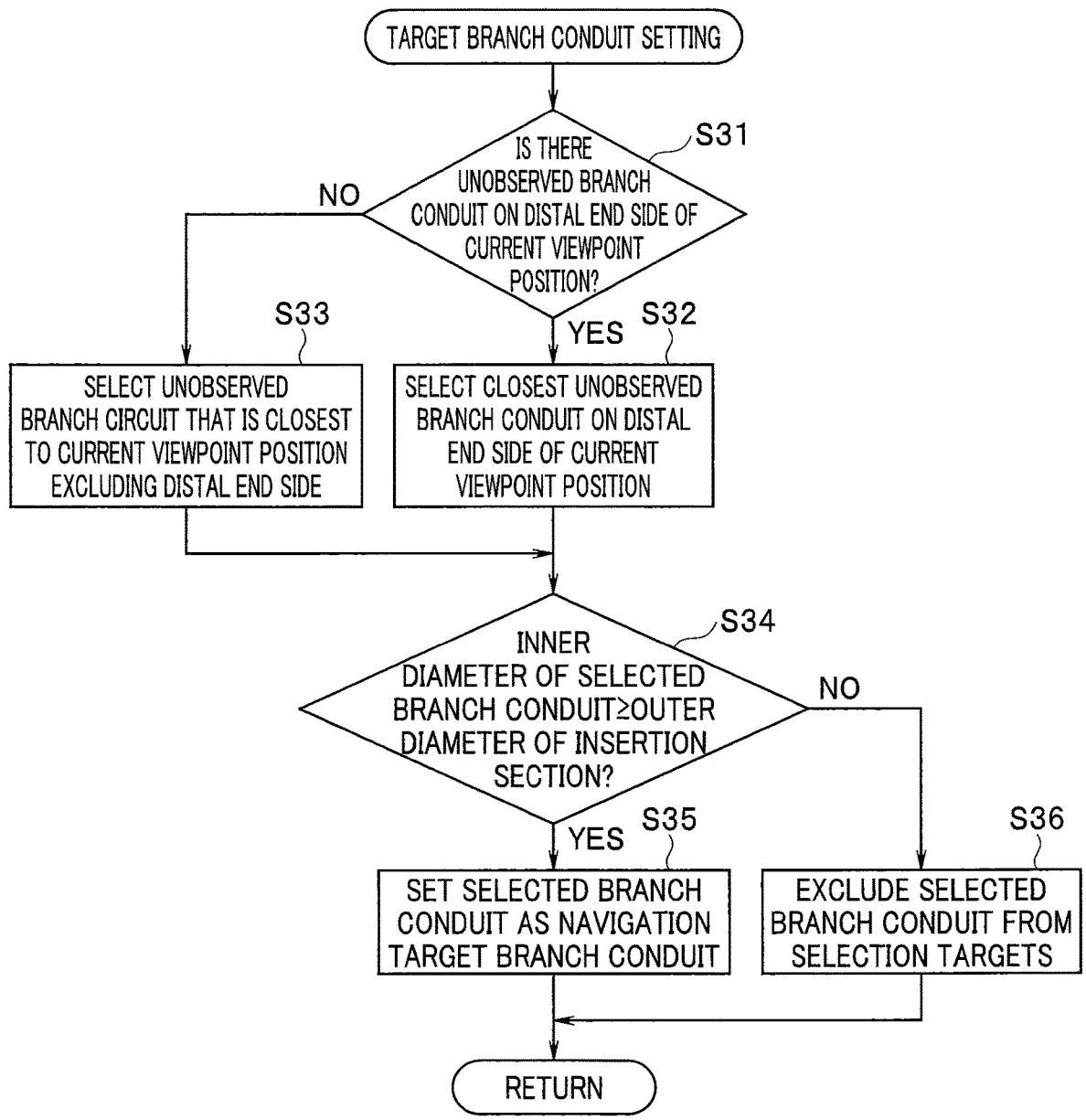
FIG. 5 is a flowchart showing target branch conduit setting processing by the endoscope system according to the first embodiment.

FIG. 5 is a flowchart showing target branch conduit setting processing by the endoscope system 1.

When the processing is started, whether an unobserved branch conduit exists on the distal end side of the current viewpoint position is determined based on the latest determination result, of the automatic observation performance determination process, stored in the determination result storage unit 36 (step S31). The distal end side here indicates not the direction of the route that is traced back by the endoscope 2 toward the proximal end portion of the endoscope 2 after tracing a route toward an unobserved branch conduit along a branch conduit in a lumen, but the direction of the endoscope 2 moving toward the distal end portion side of the current endoscope 2.

Now, in the case where existence of an unobserved branch conduit on the distal end side of the current viewpoint position is determined, the closest unobserved branch conduit on the distal end side of the current viewpoint position is selected as a selected branch conduit (step S32).

Furthermore, in step S31, if an unobserved branch conduit is determined not to exist on the distal end side of the current viewpoint position, an unobserved branch conduit that is closest to the current viewpoint position, excluding the distal end side, is selected as a selected branch conduit (step S33). The closeness at this time is determined based on the distance of the route along the branch conduit.

Then, whether the inner diameter of the selected branch conduit selected in step S32 or S33 is equal to or greater than the outer diameter of the insertion section 11, that is, whether insertion of the insertion section 11 is possible, is determined (step S34).

In the case where insertion is determined to be possible, the selected branch conduit is set as a target branch conduit of navigation (step S35).

Also, in the case where insertion is determined to be not possible in step S34, the selected branch conduit is excluded from the target branch conduit selection targets (step S36).

When step S35 or S36 is performed in the above manner, the processing returns to the processing shown in FIG. 3.

When the processing returns from the target branch conduit setting processing in step S6 to the processing shown in FIG. 3, whether a target branch conduit has been set in step S6 is determined (step S7). That is, as described above, if the processing in step S35 was performed, a target branch conduit is set, and if the processing in step S36 was performed, a target branch conduit is not yet set, and determination is performed in this regard.

If a target branch conduit is determined not to be yet set, the processing returns to step S5 described above, and whether an unobserved branch conduit exists is determined, and if an unobserved branch conduit exists, the processing in step S6 is performed again to re-set a target branch conduit.

Furthermore, in the case where a target branch conduit is determined in step S7 as already set, navigation information for guiding to the target branch conduit from the current viewpoint position is generated (step S8).

Then, whether the target branch conduit is already observed is determined based on the latest determination result stored in the determination result storage unit 36 (step S9).

Now, if the target branch conduit is determined as already observed, the processing returns to step S5, and the processing described above is repeated.

Also, if the target branch conduit is determined as not yet observed, whether the position of the target branch conduit is on the distal end side of the current viewpoint position is determined (step S10). If a surgeon is performing insertion of the insertion section 11 according to navigation, the position of the target branch conduit is supposed to be on the distal end side of the current viewpoint position, but if the surgeon performs an operation of moving off the navigation route, as in the case of inserting the insertion section 11 into a branch conduit different from the target branch conduit indicated by navigation, the position of the target branch conduit may not be on the distal end side of the current viewpoint position. Determination in step S10 is for distinguishing such a case.

Here, if the target branch conduit is determined to be on the distal end side of the current viewpoint position, the processing returns to step S9 to wait until the target branch conduit is observed.

On the other hand, in step S10, if the target branch conduit is determined as not on the distal end side of the current viewpoint position, the processing returns to step S5 described above to re-set a more appropriate target branch conduit based on the current viewpoint position.

In this manner, if an unobserved branch conduit is determined in step S5 not to exist within the predetermined region, this indicates that all the branch conduits within the predetermined region have been observed, and the process is ended (step S11) by, for example, transmission of a process end signal for the automatic observation performance determination process activated in step S3, and the processing is ended.

Figure 7:
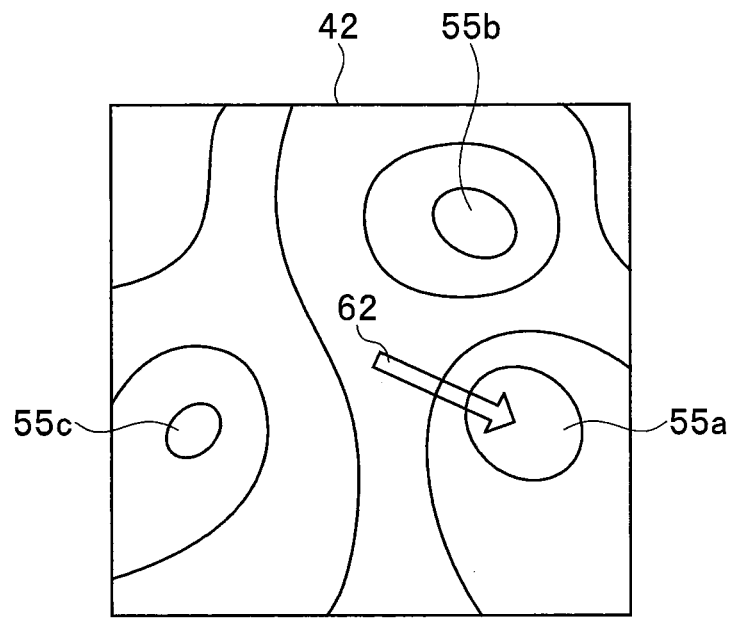
FIG. 7 is a diagram showing a state where a guide arrow to a first minor calyx in a virtual endoscopic image is displayed, according to the first embodiment.
Figure 8:
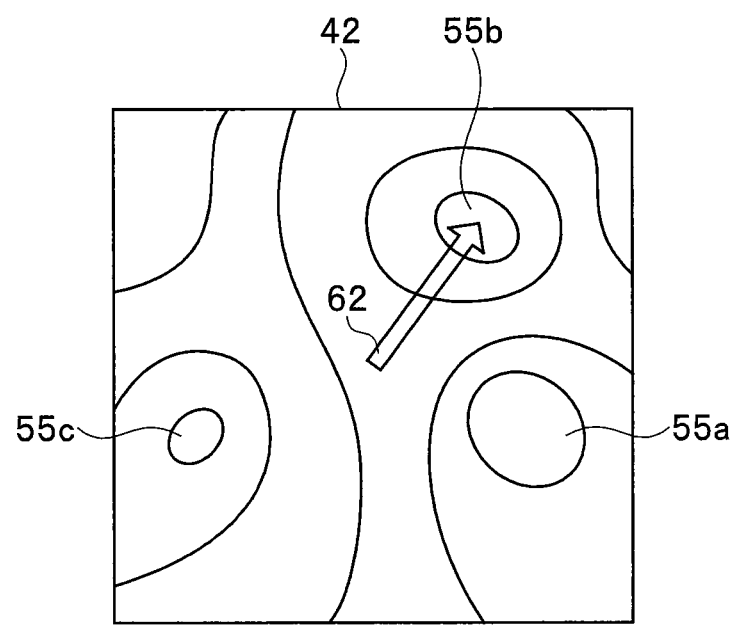
FIG. 8 is a diagram showing a state where a guide arrow to a second minor calyx in the virtual endoscopic image is displayed after observation of the first minor calyx is completed, according to the first embodiment.
Figure 9:
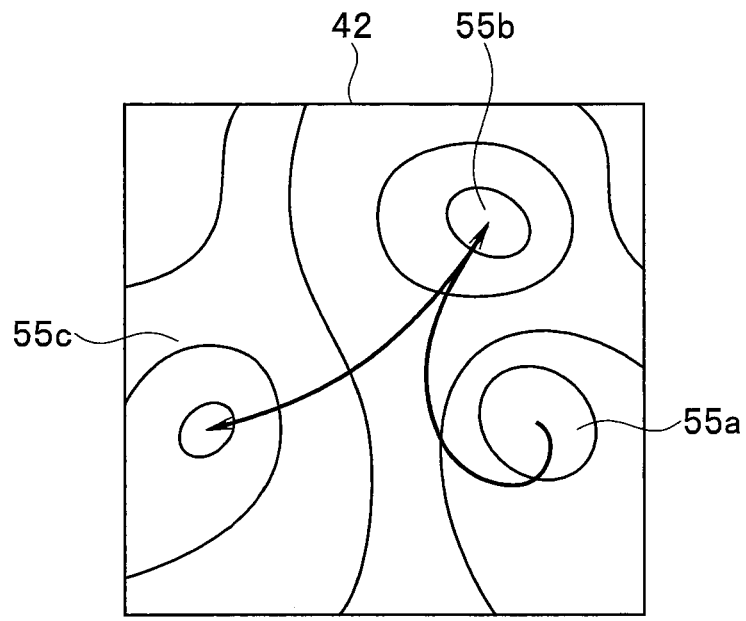
FIG. 9 is a diagram showing navigation guide moving from the first minor calyx in the virtual endoscopic image onto a third minor calyx via the second minor calyx, according to the first embodiment.

Next, FIG. 7 is a diagram showing a state where a guide arrow 62 to a first minor calyx 55a in the virtual endoscopic image 42 is displayed, FIG. 8 is a diagram showing a state where the guide arrow 62 to a second minor calyx 55b in the virtual endoscopic image 42 is displayed after observation of the first minor calyx 55a is completed, and FIG. 9 is a diagram showing navigation guide moving from the first minor calyx 55a in the virtual endoscopic image 42 onto a third minor calyx 55c via the second minor calyx 55b.

For example, as shown by the bird's-eye image 41 in FIG. 6, it is assumed that the current viewpoint position 60 of the image pickup system 10 is within the major calyx 54, and three minor calyces 55 are observed from the viewpoint position 60, as shown by the virtual endoscopic image 42 or the endoscopic image 43.

In this case, as shown in FIG. 7, the first minor calyx 55a, which is the closest unobserved branch conduit on the distal end side of the current viewpoint position 60, is set as the target branch conduit, and the guide arrow 62 is displayed in the virtual endoscopic image 42 as an example of navigation to the first minor calyx 55a set as the target branch conduit. In the example shown in FIG. 7, the guide arrow 62 is an arrow which starts from a center position, of the virtual endoscopic image 42, corresponding to the current viewpoint position 60, and ends at the first minor calyx 55a as the target branch conduit. However, the guide arrow 62 shown in FIG. 7 (and FIG. 8) is only an example of navigation display, and the display mode is not restrictive, and navigation display in other modes may also be used.

When observation of the first minor calyx 55a ends, the first minor calyx 55a becomes observed, and thus, the second minor calyx 55b, which is the closest unobserved branch conduit on the distal end side of the current viewpoint position 60, is set as the next target branch conduit, and the guide arrow 62 as shown in FIG. 8 is displayed as navigation to the second minor calyx 55b as the target branch conduit.

In this manner, guidance by navigation display sequentially moves in the order from the closest unobserved branch conduit which is on the distal end side of the current viewpoint position 60, such as from the first minor calyx 55a to the second minor calyx 55b and then to the third minor calyx 55c as shown in FIG. 9.

Figure 10:
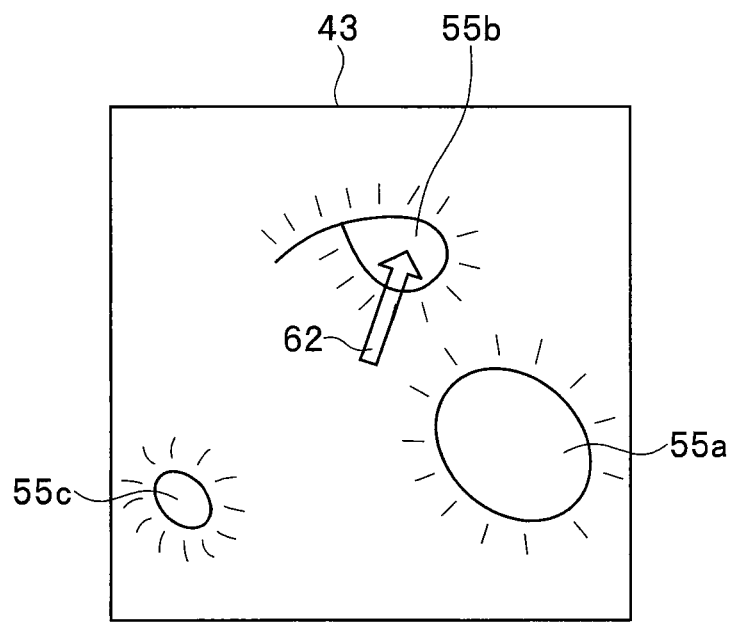
FIG. 10 is a diagram showing an example of displaying a guide arrow in an endoscopic image, according to the first embodiment.

Note that FIGS. 7 to 9 show an example of navigation display performed on the virtual endoscopic image 42, but the guide arrow 62 as an example of navigation display may also be displayed on the endoscopic image 43 as shown in FIG. 10. FIG. 10 is an example of displaying the guide arrow 62 on the endoscopic image 43. Furthermore, navigation display may also be performed on the bird's-eye image 41 without being limited to the aforementioned cases.

Figure 11:
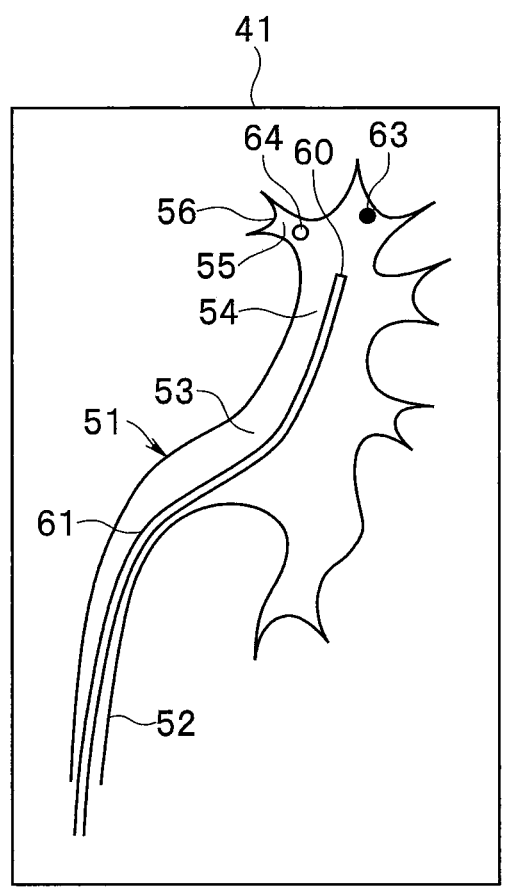
FIG. 11 is a diagram showing an example of an insertion support image displaying a target position mark and a non-insertable mark, according to the first embodiment.

Furthermore, FIG. 11 is a diagram showing an example of an insertion support image displaying a target position mark 63 and a non-insertable mark 64.

In the example shown in FIG. 11, an insertion support image is obtained by displaying the target position mark 63 and the non-insertable mark 64 on the bird's-eye image 41. Here, the target position mark 63 is a mark indicating the position of the current target branch conduit set by the processing in step S35 described above. Also, the non-insertable mark 64 is a mark indicating the position of a branch conduit that is excluded from the target branch conduit selection targets by the processing in step S36 described above. Note that insertion support information such as the target position mark 63 or the non-insertable mark 64 may alternatively be displayed on the virtual endoscopic image 42 or the endoscopic image 43.

According to the first embodiment described above, navigation information for a target branch conduit is generated by setting one of unobserved branch conduits, which are determined as unobserved, as the target branch conduit, and when the target branch conduit is determined to have been observed, updating the target branch conduit to another one of the unobserved branch conduits, and thus, an operation of sequential insertion into a plurality of branched conduits of a luminal organ is supported, and a thorough examination may be easily performed.

At this time, all the branch conduits existing within the predetermined region and which can be examined may be examined by extracting all the branch conduits existing within the predetermined region, by determining whether the insertion section may be inserted with respect to all the extracted branch conduits, and by sequentially generating the navigation information for all the branch conduits for which insertion is determined to be possible.

Furthermore, because the input unit 27, which is the region specification unit capable of specifying the predetermined region from which the branch conduits are to be extracted, is further included, a desired region may be set as the examination target.

Moreover, because an unobserved branch conduit that is closest to the current viewpoint position indicated by the corrected position information is set as the target branch conduit, the order of observation may be properly adjusted such that the amount of movement of the insertion section 11 is made small and the examination time is reduced, and thus, the efficiency of examination may be increased.

At this time, the order of observation may be optimized by setting the closest unobserved branch conduit on the distal end side of the current viewpoint position as the target branch conduit.

Furthermore, whether an unobserved target branch conduit is on the distal end side of the current viewpoint position or not is determined, and if the branch conduit is not on the distal end side of the current viewpoint position, the target branch conduit is updated based on the corrected position information, and thus, even if the current viewpoint position moves off the navigation route due to operation by the surgeon, the optimal target branch conduit at the time point may be properly set, and appropriate navigation may be constantly performed.

Then, a determination result of whether observation has been performed or not is cumulatively stored when the position indicated by the corrected position information is within the region, and the target branch conduit is set based on the latest storage contents, and thus, determination of whether a branch conduit has already been observed or not does not have to be performed every time a target branch conduit is set, and the processing load and the processing time may be reduced because unnecessary operation is omitted.

In addition, because the navigation information generation unit 34 generates the navigation information at the time of input of a command to the navigation button 12a, which is the navigation start instruction unit, the surgeon may switch between on and off of navigation display at a desired timing.

Note that a navigation system has been mainly described above, but an operation method for causing the navigation system to operate in the above manner, a program for causing a computer to realize the operation method of the navigation system, a non-transitory computer-readable recording medium recording the program are also possible.

Also, the present invention is not limited to the above-described embodiment as it is, and in the practical phase, the present invention can be embodied by modifying the structural components within the spirit of the invention. Furthermore, various aspects of the invention can be achieved by appropriately combining the plurality of structural components disclosed in the embodiment described above. For example, some structural components may be deleted from all the structural components indicated in the embodiment. Furthermore, structural components in different embodiments may arbitrarily be combined. As described above, it should be understood that various modifications and applications are possible without departing from the spirit of the invention.

What is claimed is:

1. A navigation system comprising:
a position detector configured to acquire position information of a viewpoint of an endoscope configured to be inserted in a subject; and
a processor comprising hardware, wherein the processor is configured to:
generate corrected position information in which the position information of the viewpoint of the endoscope acquired by the position detector is aligned with a three-dimensional image of a predetermined luminal organ in the subject;
determine, with respect to a plurality of branch conduits in the predetermined luminal organ, whether each of the plurality of branch conduits is already observed or is still unobserved by the endoscope, based on the corrected position information;
set, when branch conduits determined as unobserved are given as unobserved conduits, one of the unobserved conduits as a first target region, the one of the unobserved conduits being closest to a current viewpoint position of the endoscope indicated by the corrected position information and that is on a distal end side in an insertion direction of an insertion section of the endoscope, based on a distance between the position information of the viewpoint of the endoscope at a current time acquired by the position detector and the one of the unobserved conduits; and
generate navigation information for the first target region set,
wherein, when the first target region is determined as unobserved, the processor is configured to determine whether the first target region is on a distal end side of the current viewpoint position of the endoscope indicated by the corrected position information, and if the first target region is not on the distal end side of the current viewpoint position, the processor is configured to set an unobserved conduit that is closest to the current viewpoint position, among unobserved conduits excluding the first target region, as a second target region, based on the corrected position information.

2. The navigation system according to claim 1,
wherein the processor is configured to:
in a case where determination of whether the each of the plurality of branch conduits is already observed or is still unobserved by the endoscope is updated such that the first target region is already observed, set the unobserved conduit, among the unobserved conduits excluding the first target region, that is closest to the current viewpoint position of the endoscope, as the second target region; and
generate navigation information for the second target region.

3. The navigation system according to claim 1,
wherein the processor is configured to:
generate two-dimensional image data representing an optical image of an inside of the subject acquired by the endoscope; and
superimpose on the two-dimensional image data, and output to a display, the navigation information generated.

4. The navigation system according to claim 1,
wherein the processor is configured to:
control a storage to cumulatively store a result of determination of whether the each of the plurality of branch conduits is already observed or is still unobserved by the endoscope at a time when a position indicated by the corrected position information is within a predetermined region of the predetermined luminal organ; and
set the first target region based on latest storage contents of the storage.

5. The navigation system according to claim 1,
wherein the processor is configured to:
receive input of a command for starting generation of the navigation information; and
generate the navigation information from a time point of input of the command.

6. An operation method of a navigation system of an endoscope in a subject, the navigation system including a position detector and a processor comprising hardware, the operation method comprising:
acquiring, by the position detector, position information of a viewpoint of an endoscope configured to be inserted in a subject;
generating, by the processor, corrected position information in which the position information of the viewpoint of the endoscope acquired by the position detector is aligned with a three-dimensional image of a predetermined luminal organ in the subject;
determining, by the processor, with respect to a plurality of branch conduits in the predetermined luminal organ, whether each of the plurality of branch conduits is already observed or is still unobserved by the endoscope, based on the corrected position information;
setting, by the processor, when branch conduits determined as unobserved are given as unobserved conduits, one of the unobserved conduits as a first target region, the one of the unobserved conduits being closest to a current viewpoint position of the endoscope indicated by the corrected position information and that is on a distal end side in an insertion direction of an insertion section of the endoscope, based on a distance between the position information of the viewpoint of the endoscope at a current time acquired by the position detector and the one of the unobserved conduits; and
generating, by the processor, navigation information for the first target region set,
wherein, when the first target region is determined by the processor as unobserved, determining, by the processor, whether the first target region is on a distal end side of the current viewpoint position of the endoscope indicated by the corrected position information, and if the first target region is not on the distal end side of the current viewpoint position, setting, by the processor, an unobserved conduit that is closest to the current viewpoint position, among unobserved conduits excluding the first target region, as a second target region, based on the corrected position information.

7. A navigation system comprising:

a position detector configured to acquire position information of a viewpoint of an endoscope configured to be inserted in a subject; and a processor comprising hardware, wherein the processor is configured to:

generate corrected position information in which the position information of the viewpoint of the endoscope acquired by the position detector is aligned with a three-dimensional image of a predetermined luminal organ in the subject;

determine, with respect to a plurality of branch conduits in the predetermined luminal organ, whether each of the plurality of branch conduits is already observed or is still unobserved by the endoscope, based on the corrected position information;

set one of the plurality of branch conduits as a first target region, based on a distance between the position information of the viewpoint of the endoscope at a current time acquired by the position detector and the plurality of branch conduits; and generate navigation information for the first target region, when the first target region set is determined as unobserved, wherein, when the first target region is determined as unobserved, the processor is configured to determine whether the first target region is on a distal end side of the current viewpoint position of the endoscope indicated by the corrected position information, and if the first target region is not on the distal end side of the current viewpoint position, the processor is configured to set an unobserved conduit that is closest to the current viewpoint position, among unobserved conduits excluding the first target region, as a second target region, based on the corrected position information.

8. The navigation system according to claim 7, wherein the processor is configured to:

when the first target region is determined as already observed, set the unobserved conduit that is closest to the current viewpoint position of the endoscope, among the unobserved conduits excluding the first target region, as the second target region; and generate navigation information for the second target region.

* * * * *